United States Patent
Ke et al.

(10) Patent No.: US 12,161,413 B2
(45) Date of Patent: Dec. 10, 2024

(54) SYSTEMS AND METHODS FOR CORNEAL PROPERTY ANALYSIS USING TERAHERTZ RADIATION

(71) Applicants: AGENCY FOR SCIENCE, TECHNOLOGY AND RESEARCH, Singapore (SG); Singapore Health Services PTE LTD, Singapore (SG)

(72) Inventors: Lin Ke, Singapore (SG); Hongwei Liu, Singapore (SG); Nan Zhang, Singapore (SG); Jod S Mehta, Singapore (SG); Yu Chi Liu, Singapore (SG)

(73) Assignees: Agency for Science, Technology and Research, Singapore (SG); Singapore Health Services PTE Ltd, Singapore (SG)

(*) Notice: Subject to any disclaimer, the term of this patent is extended or adjusted under 35 U.S.C. 154(b) by 943 days.

(21) Appl. No.: 17/260,218

(22) PCT Filed: Jul. 10, 2019

(86) PCT No.: PCT/SG2019/050337
§ 371 (c)(1),
(2) Date: Jan. 13, 2021

(87) PCT Pub. No.: WO2020/013762
PCT Pub. Date: Jan. 16, 2020

(65) Prior Publication Data
US 2021/0298594 A1 Sep. 30, 2021

(30) Foreign Application Priority Data
Jul. 13, 2018 (SG) .......................... 10201806046S (51) Int. Cl.
*A61B 3/107* (2006.01)
*A61B 5/0507* (2021.01)
(Continued)

(52) U.S. Cl.
CPC ............ *A61B 3/107* (2013.01); *A61B 5/0507* (2013.01); *G16H 20/40* (2018.01); *G16H 50/30* (2018.01)

(58) Field of Classification Search
CPC ...... A61B 3/107; A61B 5/0507; G16H 20/40; G16H 50/30
See application file for complete search history.

(56) References Cited

U.S. PATENT DOCUMENTS

| 5,636,635 A | * | 6/1997 | Massie | ................... | A61B 3/165 |
| | | | | | 600/587 |
| 7,641,343 B1 | * | 1/2010 | Motamedi | .............. | A61B 3/102 |
| | | | | | 351/205 |
| 2012/0265047 A1 | | 10/2012 | Yen | | |

OTHER PUBLICATIONS

Sung, Shijun, et al. "Direct measurement of corneal tissue water content by reflection imaging at Terahertz Frequencies." Investigative Ophthalmology & Visual Science 56.7 (2015): 1644-1644. (Year: 2015).*

(Continued)

*Primary Examiner* — Sean D Mattson
(74) *Attorney, Agent, or Firm* — Womble Bond Dickinson (US) LLP (57) ABSTRACT

Methods and systems for analysing a property of a cornea of an eye using terahertz (THz) radiation are provided. The method includes projecting a first THz wave onto a surface of the cornea and detecting a first reflected wave being a reflection of the first THz wave reflected from the surface of the cornea. The method further includes deforming the cornea, projecting a second THz wave onto the surface of the cornea after the deforming and detecting a second reflected wave being a reflection of the second THz wave reflected from the surface of the cornea after the deforming. Finally, (Continued)

the method includes calculating the property of the cornea based on the first reflected wave and the second reflected wave.

22 Claims, 6 Drawing Sheets

(51) Int. Cl.
*G16H 20/40* (2018.01)
*G16H 50/30* (2018.01)

(56) References Cited

OTHER PUBLICATIONS

Taylor, Zachary D., et al. "THz and mm-wave sensing of corneal tissue water content: in vivo sensing and imaging results." IEEE transactions on terahertz science and technology 5.2 (2015): 184-196. (Year: 2011).*

Correas-Serrano, Diego, and J. Sebastian Gomez-Diaz. "Graphene-based antennas for terahertz systems: a review." arXiv preprint arXiv: 1704.00371 (2017) (Year: 2017).*

International Preliminary Report on Patentablity from Singapore International Application No. PCT/SG2019/050337, issued Jan. 19, 2021, 4 pages.

International Search Report from Singapore International Application No. PCT/SG2019/050337, mailed Feb. 9, 2019, 3 pages.

Dorronsoro et al., "Dynamic OCT measurement of corneal deformation by an air puff in normal and cross-linked corneas," Biomedical Optics Express, Feb. 9, 2012, vol. 3, No. 3, pages e473: 1-15 [Retrieved on Aug. 19, 2019] <DOI: 10.1364/BOE.3.000473> whole document.

Taylor et al., "THz Medical Imaging: in vivo Hydration Sensing," IEEE Trans Terahertz Sci Technol., Sep. 30, 2011, vol. 1, No. 1, pp. 201-219 [Retrieved on 2019-0-19] <DOI: 10.1109/TTHZ.2011. 2159551> sections IV-VII; fig. 7-8; 18.

Yoon et al., "Stiffness measurement using terahertz and acoustic waves for biological samples," Optics Express, Dec. 10, 2015, vol. 23, No. 25, pp. 32671-32678 [Retrieved on Aug. 19, 2019] <DOI: 10.1364/OE.23.032671> fig. 1-2; sections 1-2.

Written Opinion of the International Searching Authority from Singapore International Application No. PCT/SG2019/050337, mailed Feb. 9, 2019, 6 pages.

* cited by examiner

SYSTEMS AND METHODS FOR CORNEAL PROPERTY ANALYSIS USING TERAHERTZ RADIATION

CROSS-REFERENCE TO RELATED APPLICATIONS

This patent application is a U.S. National Phase Application Under 35 U.S.C § 371 of International Application No. PCT/SG2019/050337, filed 10 Jul. 2019, entitled "SYSTEMS AND METHODS FOR CORNEAL PROPERTY ANALYSIS USING TERAHERTZ RADIATION," which claims the benefit of priority of Singapore patent application Ser. No. 10/201,806046S, filed on 13 July 2018.

TECHNICAL FIELD

The present invention relates to corneal property analysis, and more particularly relates to systems and methods for corneal elasticity and/or rigidity analysis using terahertz (THz) time-domain spectroscopy.

BACKGROUND OF THE DISCLOSURE

Ocular rigidity (OR) of eyeballs is affected not only by outer ocular coats (i.e. sclera and cornea), but also by the choroid and the status of ocular blood circulation. The rigidity may be altered by surgical procedures affecting the ocular walls, such as refractive procedures. Based on previous studies, the rigidity may, in turn, affect the accuracy of measurements of the intraocular pressure (IOP) as well as the pathogenesis of various ophthalmic conditions, such as glaucoma or age-related macular degeneration (AMD).

Therefore, what is desired is in vivo or ex vivo methods to obtain accurate corneal rigidity measurement. However, there are currently no satisfactory in vivo or ex vivo methods in corneal elastic/rigidity measurement and/or structure change measurement. Known methods are intrusive and usually take a long time to perform the measurement which causes pain to patients during in vivo corneal elastic/rigidity measurement.

Thus, there is a need for methods and systems that are non-intrusive, painless and rapid and are able to solve the above-mentioned shortcomings of the prior art while providing further additional advantages. Furthermore, other desirable features and characteristics will become apparent from the subsequent detailed description and the appended claims, taken in conjunction with the accompanying drawings and this background of the disclosure.

SUMMARY

According to at least one embodiment of the present invention, a method for analysing a property of a cornea of an eye using terahertz (THz) radiation is provided. The method includes projecting a first THz wave onto a surface of the cornea and detecting a first reflected wave being a reflection of the first THz wave reflected from the surface of the cornea. The method further includes deforming the cornea, projecting a second THz wave onto the surface of the cornea after the deforming and detecting a second reflected wave being a reflection of the second THz wave reflected from the surface of the cornea after the deforming. Finally, the method includes calculating the property of the cornea based on the first reflected wave and the second reflected wave.

According to another embodiment of the present invention, a system for analysing a property of a cornea of an eye using terahertz (THz) radiation is provided. The system includes a device configured to deform the cornea, a terahertz radiation measuring system and a signal processing unit. The terahertz radiation measuring system includes a terahertz radiation generator and a terahertz radiation detector. The terahertz radiation generator is configured to project a first THz wave and a second THz wave respectively before and after the corneal deforming. The terahertz radiation detector is configured to detect a first reflected wave being a reflection of the first THz wave reflected from the surface of the cornea and detect a second reflected wave being a reflection of the second THz wave reflected from the surface of the cornea after the deforming. And the signal processing unit is configured to communicate with the terahertz radiation measuring system to calculate the property of the cornea based on the first reflected wave and the second reflected wave.

According to a further embodiment of the present invention, a computer readable medium providing instructions for a system to perform a method for analysing a property of a cornea of an eye using terahertz (THz) radiation is provided. The computer readable medium includes instructions for the system to project a first THz wave onto a surface of the cornea and detect a first reflected wave being a reflection of the first THz wave reflected from the surface of the cornea. The computer readable medium further includes instructions for the system to deform the cornea, project a second THz wave onto the surface of the cornea after the deforming and detect a second reflected wave being a reflection of the second THz wave reflected from the surface of the cornea after the deforming. Finally, the computer readable medium includes instructions for the system to calculate the property of the cornea based on the first reflected wave and the second reflected wave.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

Skilled artisans will appreciate that elements in the figures are illustrated for simplicity and clarity and have not necessarily been depicted to scale.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of the present embodiment to present methods and systems for analysing properties of a cornea of an eye using terahertz (THz) radiation which uses a predetermined wavelength of light to stress the cornea to trigger elastic changes and using terahertz radiation to observe the corneal structure change before and after the light stress thereby providing a non-intrusive, painless and rapid system and method to obtain reliable cornea elastic constant and rigidity parameter measurements.

Rigidity describes the mathematical relationship between the volume tended by a confined structure filled with incompressible contents such as fluid and the pressure inside the structure. Thus, rigidity reflects the elastic properties of the structure walls. However, in the case of an eyeball, ocular rigidity (OR) is affected not only by the outer ocular coats such as the sclera and the cornea, but also by the choroid and the status of ocular blood circulation. In addition, OR may be altered by surgical procedures affecting the ocular walls such as refractive surgical procedures.

Conventional measurement techniques have shown that OR may affect accuracy of intraocular pressure and pathogenesis of various ophthalmic conditions such as glaucoma or age-related macular degeneration. Although a variety of methods have been employed for quantitative determination of OR, technical difficulties in obtaining accurate in vivo measurements have limited the clinical role of systems and methods for OR determination.

While recent advances have enabled accurate real-time measurements of OR enabling potential incorporation of ocular rigidity measurement in ophthalmic diagnosis and decision-making for treatment, there are significant drawbacks which limit conventional OR measurement systems. For example, intraoperative anterior chamber manometry based on the suggestion that OR is altered in enucleated eyes suffers from inaccuracies because only rigidity is measured.

Axial length-associated OR measurement measures ocular axial length changes induced by, for example, oral administration of acetazolamide with partial coherence laser interferometry. The acetazolamide reduces the intraocular pressure and this pressure reduction can be measured with dynamic contour tonometry before and about two hours after the acetazolamide intake. The resulting axial length decrease per intraocular pressure reduction is then used to estimate ocular rigidity, however this measurement process over two hours takes a long time and results in significant patient suffering.

Another indirect approach to measure OR has been based on the combined assessment of Fundus Pulse Amplitude and Ocular Pulse Amplitude where the Ocular Pulse Amplitude corresponds to the maximum IOP change during the cardiac cycle. This measurement process is intrusive and takes a long time because the doctors and ophthalmologists have to wait to observe the ocular pulse amplitude as it fully dissipates while capturing the readings during the process. This measurement process causes inconvenience for both patients and ophthalmologists.

Corneal hysteresis, measured with an ocular response analyzer, such as an ORA, manufactured by Reichert Inc. of Buffalo, NY, USA, reflects viscous damping in the cornea (i.e., the capacity of corneal tissue to recover their shape following application of external forces). The ocular response analyzer releases a precisely metered air pulse that causes the cornea to move inward, the air pulse successively passing inward through the cornea and then outward. Like the assessment of Fundus Pulse Amplitude and Ocular Pulse Amplitude, measurement of corneal hysteresis process is intrusive and takes a long time, causing patients and ophthalmologists inconvenience.

The importance of an accurate quantitative assessment of the elastic structural properties of the eye has led to suggestions that ultrasound elastography may also be used as a tool for real-time in vivo measurements of OR, however there are currently no ultrasound elastography systems available or methods developed. This, there are currently no satisfactory in-vivo cornea elastic/rigidity and structure change measurement methods Present embodiments address the drawbacks of the prior art system and methods by providing a rapid, non-destructive, and non-contact technology for measuring corneal rigidity and elastic. Embodiments of systems and methods of the present invention operate in the THz range in the electromagnetic spectrum which lies between microwave and infrared frequencies and generally defines frequencies ranging from 100 GHz ($10^{11}$ Hz, 3 mm wavelength) to 10 THz ($10^{13}$ Hz, 3.3 µm wavelength). Electromagnetic radiation in the THz range may also be referred to as THz light, THz radiation, or THz waveforms.

Figure 1:
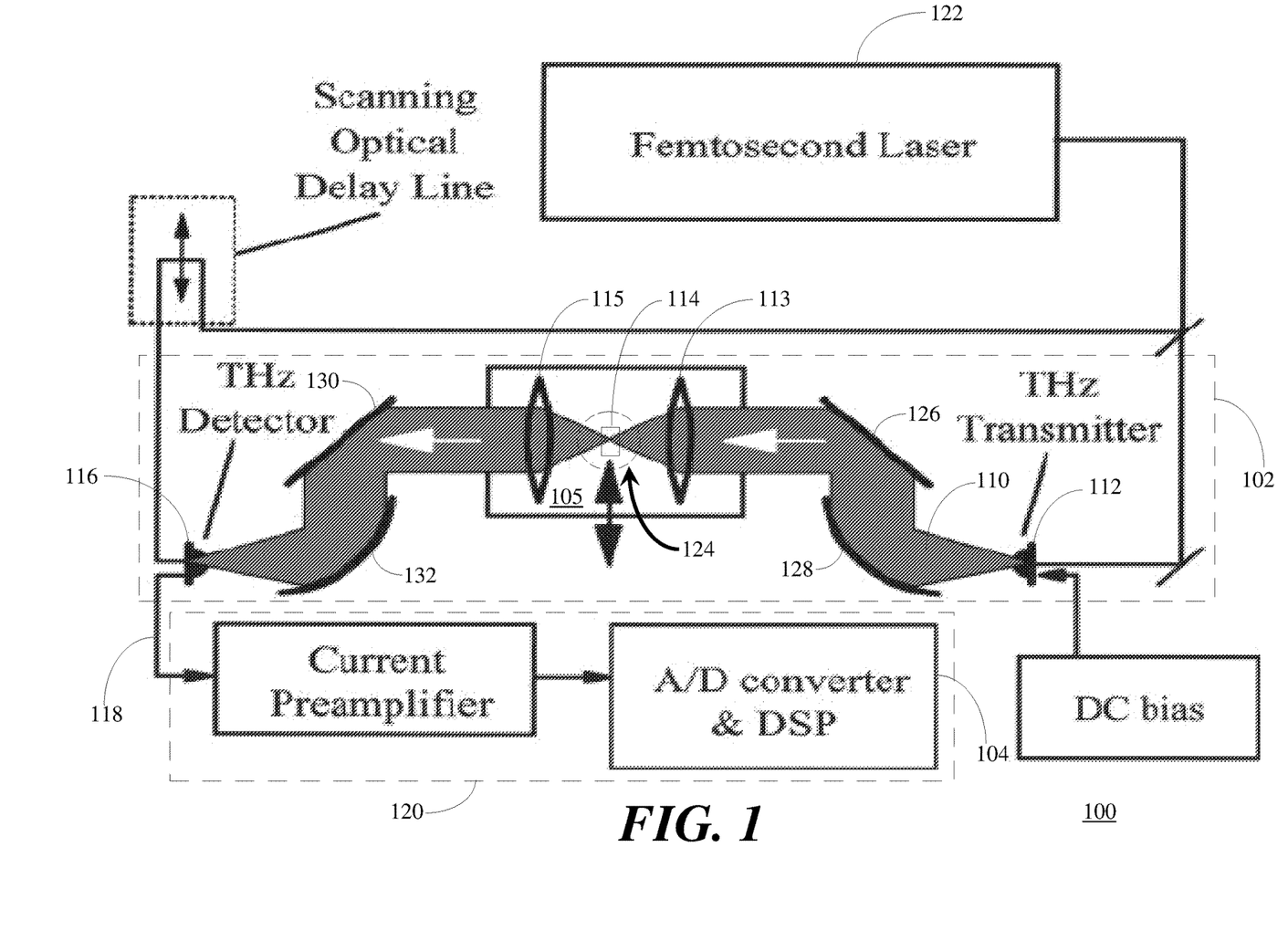
FIG. 1 depicts an illustration of a system for analysing properties of a cornea of an eye using terahertz (THz) radiation in accordance with present embodiments.

In accordance with present embodiments, a system, such as a terahertz portable system, analyses corneal elasticity and rigidity ex-vivo and in-vivo using terahertz time-domain spectroscopy. Referring to FIG. 1, an illustration 100 of a system for analysing corneal elasticity and rigidity of an eye using terahertz (THz) radiation in accordance with present embodiments uses a THz time-domain (THz-TDS) system 102, a computer or other processing means 104.

The THz-TDS system 102 can be configured to reflect electromagnetic radiation 110 in THz range from a THz transmitter or emitter 112 toward a surface of an eye 114, receive THz light reflected from the eye at a THz detector or receiver 116, and generate a signal 118 indicative of the received radiation which is amplified and digitized by circuitry 120. The THz radiation is generated by the THz transmitter 112, such as an antenna or a nonlinear crystal, and pulsed in response to a signal from a femtosecond laser 122. The THz detector or receiver 116 can also be an antenna or a nonlinear crystal. The computer 104, which communicates with THz-TDS system 102, can be configured to process the generated signal 118 and may further be configured for creating a visual imaging of the THz response from the surface of the eye 114. A XYZ stage 105 can be configured to manipulate the structure of the THz-TDS system 102 to scan the surface of the eye 114 and move THz focal point 124 from a surface of the eye 114 to a level below the surface of the eye.

Thus, the system 100 for corneal rigidity and elastic analysis includes an illumination system (e.g., the femtosecond laser 122 and the THz transmitter 112) configured to provide an illumination beam of terahertz radiation 110, an optical system including mirrors and lenses (e.g., lens 113) arranged in an optical path of the terahertz radiation 110 to relay and direct at least a portion of the illumination beam of terahertz radiation 110 onto a cornea 114 of a subject and to receive at least a portion of terahertz radiation reflected from said cornea to provide a return beam of terahertz radiation, and a detection system (e.g., detector 116) arranged in an optical path of said return beam of terahertz radiation, the detection system configured to provide a detection signal 118 from detecting at least a portion of said return beam of terahertz radiation. A signal processing system 120 is configured to communicate with the detection system 116 to receive the detection signal 118, wherein the signal processing system processes the detection signal to provide a measure of elastic and rigidity in the cornea 114 of the subject.

As seen from FIG. 1, the illumination system comprises a THz generator head including the femtosecond laser 122 and a nonlinear optical crystal (i.e., the THz transmitter 112-112). The optical system is configured to focus oblique-angle illumination of terahertz radiation on the subject's cornea 114 at the focal point 124. The illumination optical system, which can be open space or fiber connected, includes a pair of off-axis parabolic mirrors 126, 128 and a pick-up optical system configured to provide the return beam of terahertz radiation also includes a pair of off-axis parabolic mirrors 130, 132. The detection system 116 is configured to detect said return beam of terahertz radiation within a frequency band of about 0.1 THz to about 10 THz.

Figure 2:
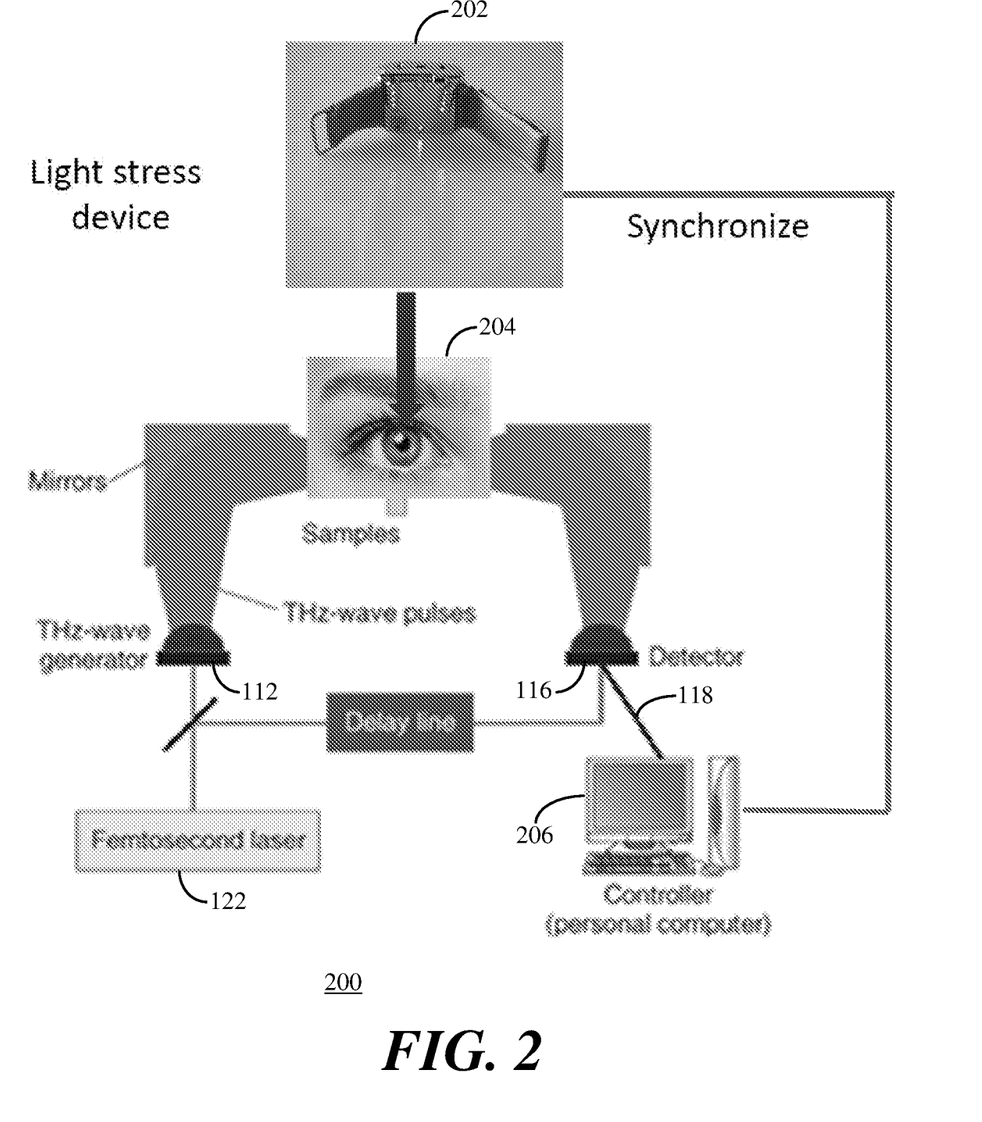
FIG. 2 depicts an illustration of the system of FIG. 1 including a light stress device for performing corneal property analysis in accordance with the present embodiments.

One of objectives of the present embodiments is to provide a non-contact system for measuring corneal mechanical properties and a method for measuring corneal elasticity. Referring to FIG. 2, an illustration 200 depicts use of the system 100 and a light stress device 202 for performing corneal property analysis of a subject's eye 204 in accordance with the present embodiments. To achieve the above objective, the present embodiments provide a non-contact system for measuring corneal mechanical properties of the subject's eye 204, which includes a light-pressure device 202, which provide a light toward a cornea of a live eyeball from about a distance of one or two centimeters in front of the eyeball and measures light pressure thereof. The light-pressure device 202 is configured to deform the cornea, preferably for less than ten seconds, and can be a red light having a wavelength of 632 nm generated by the light-pressure device at a power of 100μW. Another corneal deformation device could also be used, such as an air-puffing device. The terahertz radiation measuring system (THz-TDS) includes the THz wave generator 112 and the THz detector 116 and generates terahertz radiation before and after the light-pressure device 202 applies stress on the surface of cornea for measuring corneal deformation caused by the light applied to the cornea. The signal processing unit 120, including computer 206 which controls the system by, for example, synchronizing operation of the light-pressure device 202 and the terahertz radiation measuring system (THz-TDS), as well as calculating the elastic constant by utilizing the corneal deformation measured by the terahertz radiation and the measured light pressure.

The ability of a material to resist deformation reflects either its modulus of rigidity under shearing or twisting stress or its modulus of elasticity under stretching stress. The modulus of rigidity, or shear modulus, measures stiffness. When an object experiences a force parallel to its length that is greater than its strength, it either slides against the source of the stress, or it slides internally, causing small changes to its volume. The modulus of elasticity measures springiness. When an object is pulled perpendicularly to its length by strong forces, it reaches a point where it cannot return to its original dimensions. Young's modulus is one type of the modulus of elasticity.

The modulus of rigidity is valid for both elastic and non-elastic deformations while modulus of elasticity is only valid for elastic deformations. Elastic deformation is defined for forces normal to the surface while modulus of rigidity is defined for forces acting along the surface parallel to it. The deformation for the modulus of elasticity is linear while the deformation for the modulus of rigidity is a circular one.

Once there is a force (for example, a light source) on a surface, there could be dimensional changes both along the surface and perpendicular the surface. Thereafter, there is a relationship between the modules of the rigidity and modules of the elasticity. The relationship between modules of the rigidity (G) and modules of the elastic (E) is governed by Equation (1).

$$E = 2G(1+v) \tag{1}$$

wherein v represents a number called Poisson's ratio. The properties of the cornea such as elasticity are derived from a force-motion relationship as shown in Equation (2).

$$F = cx \tag{2}$$

In this embodiment, x can be derived from the THz peak position change before and after a visible light beam is shined on the cornea to provide stress where F is the light pressure (i.e., stress) given by the visible light as seen in Equation (3).

$$F = (1+p)E/C \tag{3}$$

where p is reflection coefficient, E is incident energy flux in $W/m^2$, and C is the speed of light in a vacuum.

In Equation (2), c represents a spring constant, and once force F and deformation x are confirmed, then c can be calculated. More properties can be added for Equation (2) for more complex systems, which is closer to a real system as shown in Equation (4).

$$F = cx + nx' + mx'' \tag{4}$$

where n represents a damping factor and m represents mass.

Figure 3:
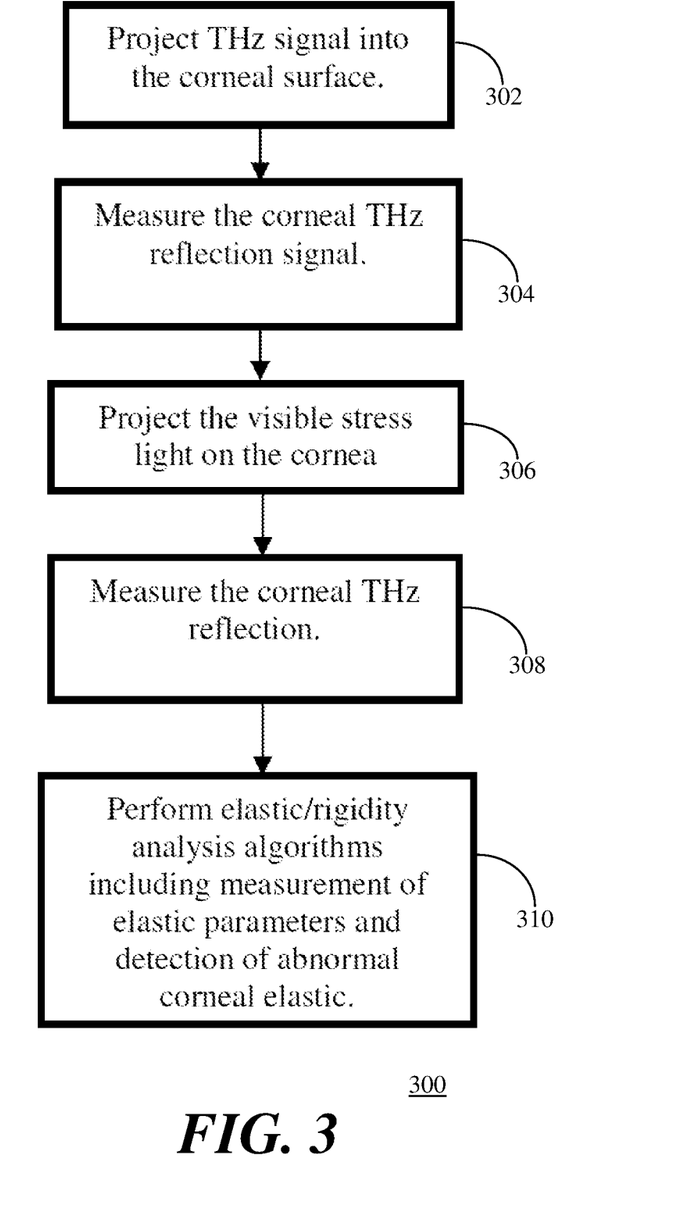
FIG. 3 depicts a flow chart of a method for analysing corneal properties of an eye using terahertz radiation in accordance with the present embodiments.

FIG. 3 depicts a flowchart 300 of an exemplary method for cornea elasticity/rigidity measurement in accordance with the present embodiments. The method includes projecting THz radiation onto the corneal surface 302. The reflected THz signal arriving at the detector 116 is measured a first time 304. Then, the visible stress light 202 is projected 306 onto the cornea and the reflected THz signal arriving at the detector 116 is measured a second time 308. The corneal elasticity and rigidity are calculated 310 by perform elastic/rigidity analysis algorithms of the two measurements to derive corneal elastic parameters and detect of abnormalities of the corneal elasticity.

This technology can be useful in patients who are undergoing laser refractive surgery. Monitoring of the corneal components during refractive surgery to adjust the femtosecond laser operating conditions can improve the successful rate of the operations. With current refractive surgery, the only parameter which is not precisely accessed is the cornea rigidity, which is believed to be the affecting factor for the current gap. With the present technology developed, the cornea properties, stromal components concentration, corneal elastic/rigidity etc.; can be instantly measured as the input for the laser operation conditions.

This technology can also be useful for the patients with dry eyes. The doctors could monitor the tear film performance, therapeutic response and analysis the dry eye formation. The technology is useful in patients with corneal edema from infections or other degenerative conditions and can contribute to the early diagnosis, treatment and monitoring of various corneal diseases.

The present invention is able to observe dynamic behaviour of the corneal which shows the dynamic changes of the corneal after the stress. From the THz spectroscopy, the present invention is able to continuously observe the dynamic changes of the corneal or even observe the recovery of the corneal after the stress.

The information obtained could help in the design of non-invasive cornea elastic and ocular rigidity (OR) measurement modalities, such as ophthalmic elastography systems, applicable in the everyday clinical practice, which could be used in the study of a variety of ophthalmic conditions, including glaucoma, age-related macular degeneration, changes induced in the eye by refractive surgery as well as in the study for presbyopia.

Figure 4:
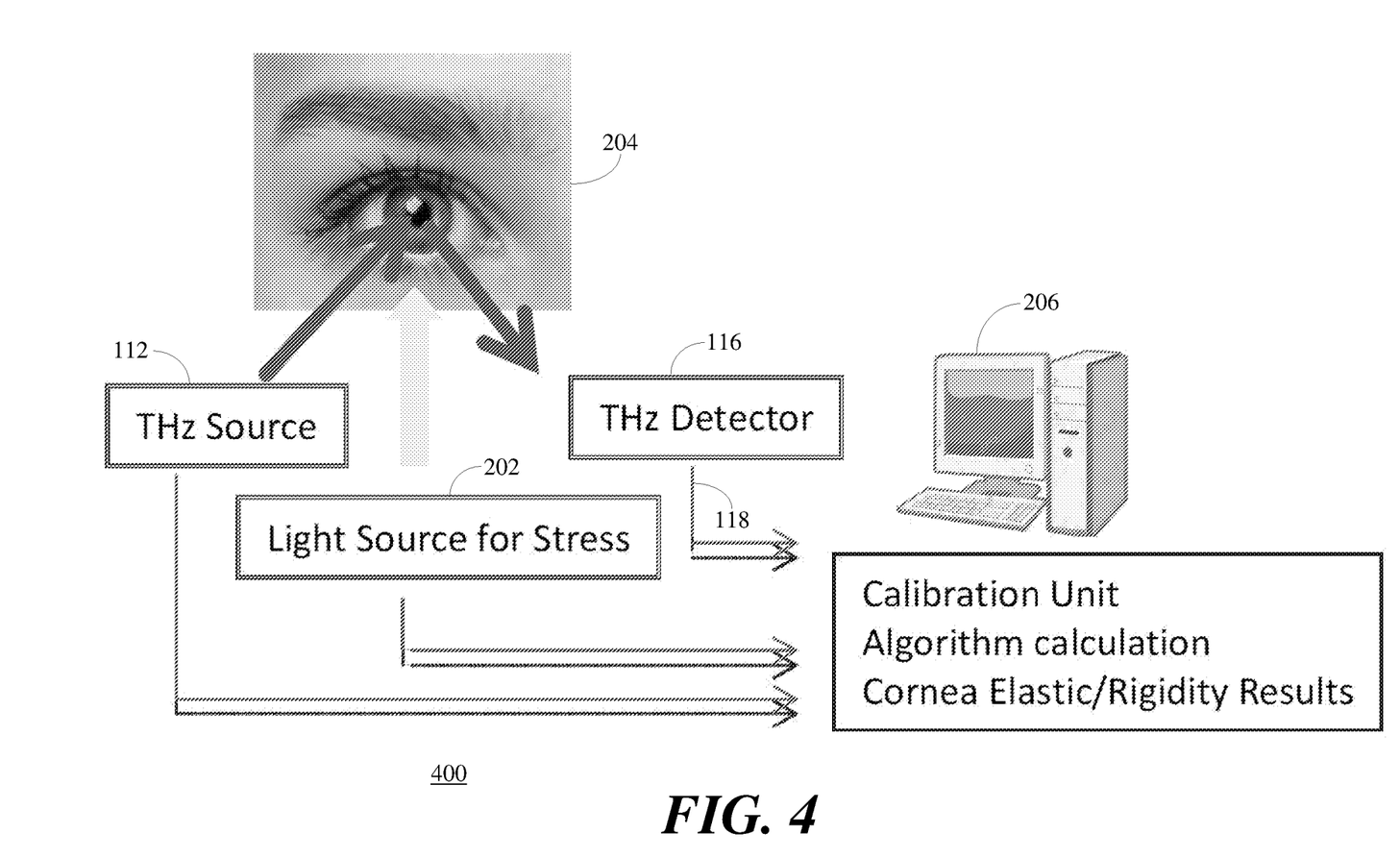
FIG. 4 depicts a schematic diagram for operation of the system of FIG. 2 in accordance with the present embodiments.

Referring to FIG. 4, a schematic diagram 400 depicts operation of the system 200 in accordance with the present embodiments. The external perturbation caused by the light stress from the light source 202 induces a light pressure on the surface of cornea 204. As the rigidity and elasticity of the cornea 204 is different for each cornea based on its current condition, the same light stress will cause various corneal deformations and the corneal deformation leads to the change of the THz time delay between the first measurement 304 and the second measurement 308.

Figure 5:
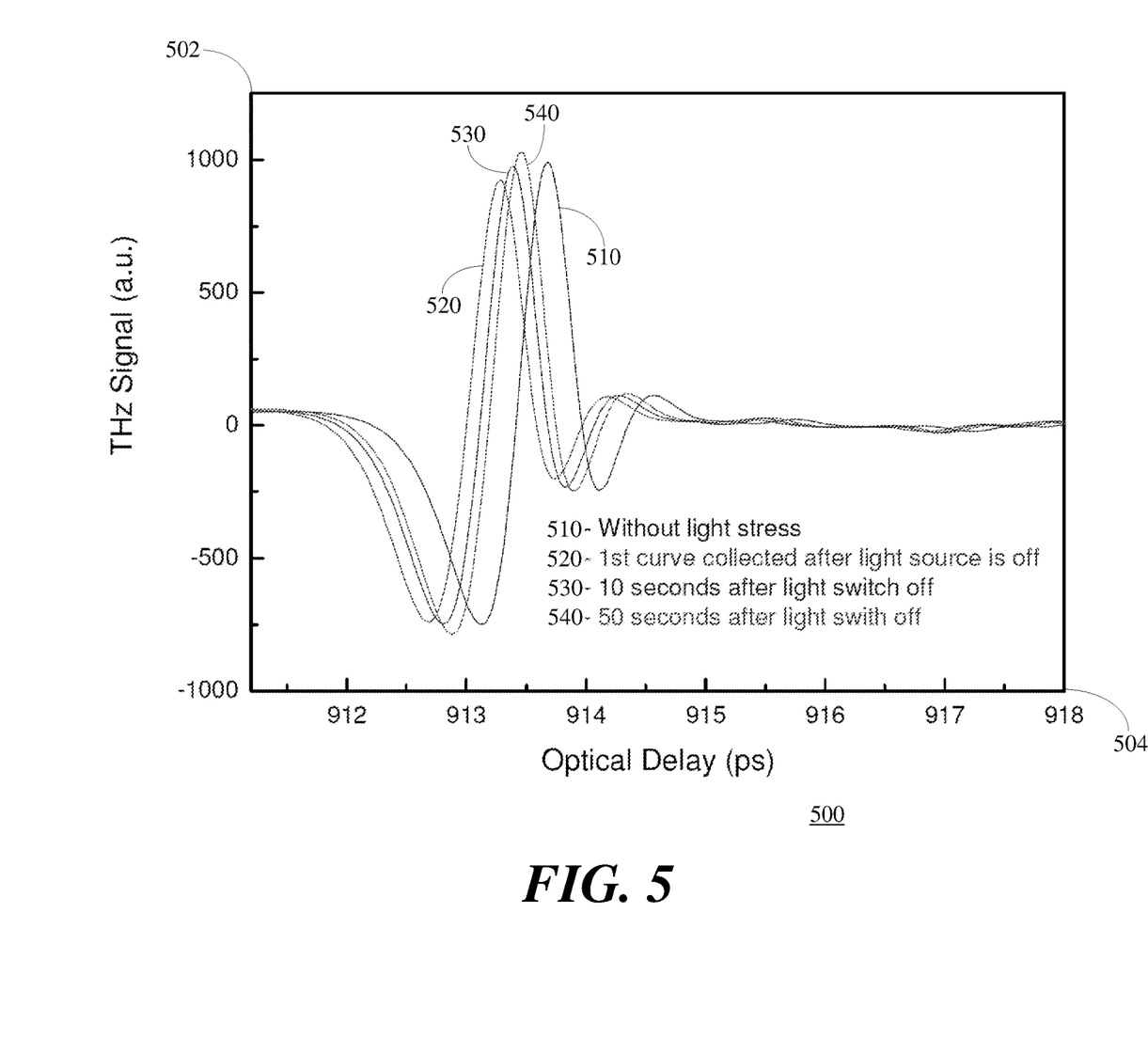
FIG. 5 depicts a graph of results of corneal property measurements for a light stressed porcine eye in accordance with the present embodiments.

This can be seen in the graph 500 of FIG. 5. The graph 500 depicts results of corneal property measurements for a light stressed porcine eye in accordance with the present embodiments. The THz signal amplitude is measured along the y-axis 502 while the optical delay is measured along the x-axis 504. In a first curve 510, the THz signal is been collected on the surface of the corneal without light.

A 632 nm red light of 100 µW source is then shone on the surface of the corneal for 5 seconds. A second curve 520 depicts the THz signal collected immediately after the light source is turned off. The THz signals are thereafter continuously collected to monitor the corneal changes. A third curve 530 depicts the THz signals collected ten seconds after the light is turned off and a fourth curve 540 depicts the THz signals collected fifty seconds after the light is turned off. The recovering of THz signal has been detected, which shows that the red light source did not cause any permanent damage to the cornea.

When the light source 202 is turned on, the time delay of THz signal shifts instantly, indicating deformation of the cornea. The difference between the curves with no light stress and the 1st curve collected immediately after the light source is off is due to the corneal deformation induced by the light stress. By monitoring the differences, the cornea elastic/rigidity properties can be determined.

Figure 6:
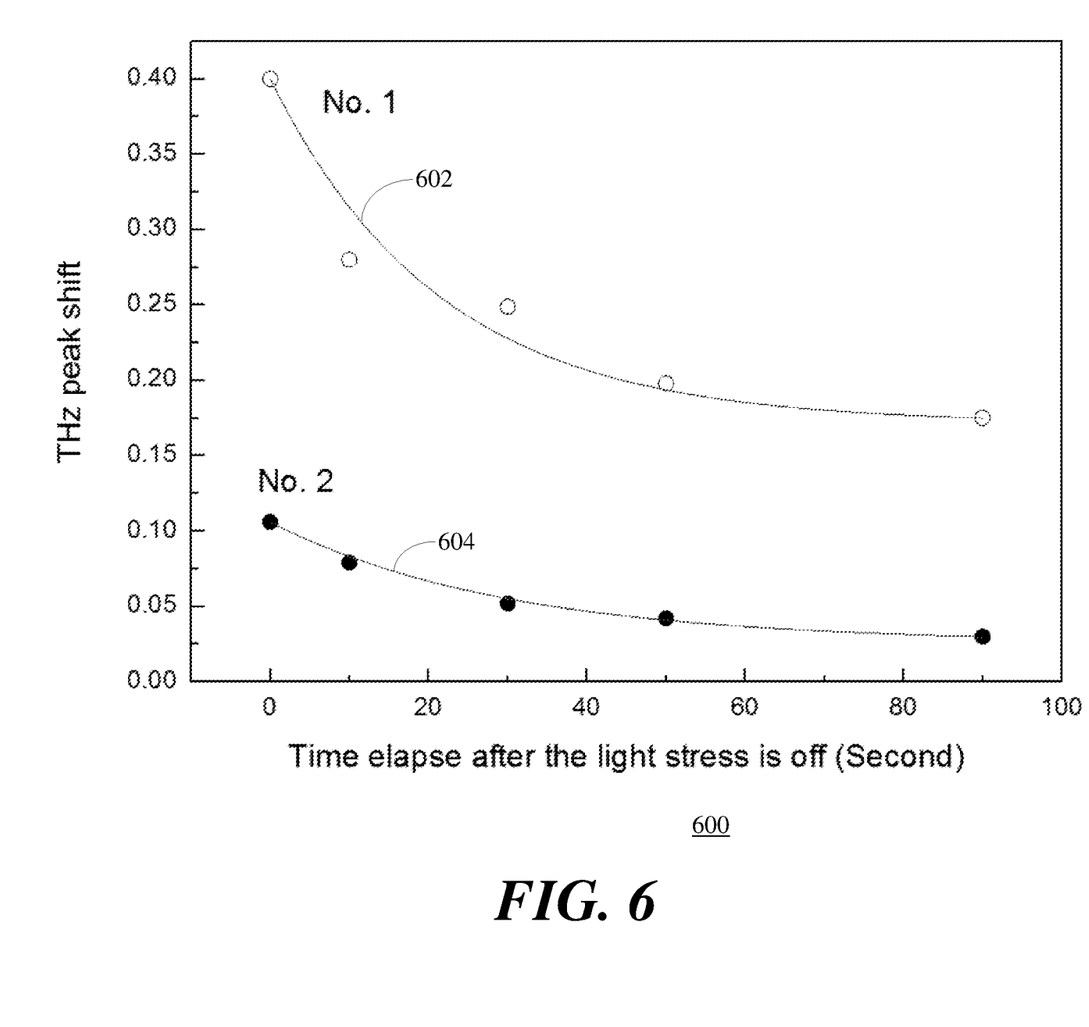
FIG. 6 depicts a graph of terahertz signals of two porcine eye samples measured in accordance with the present embodiments.

Referring to FIG. 6, a graph 600 depicts terahertz signals of two porcine eye samples 602, 604 measured to show the THz signals comparison before and after light stress in accordance with the present embodiments. The two porcine eye samples 602, 604 demonstrate different THz displacement under the same light stress. The recovering speed also shows the measurable difference.

The exponential decay fitting parameters for sample 602 and sample 604 are: Y=0.1716+0.1142exp (−t/21.3936) and Y=0.02619+0.0399exp (−t/29.58277), respectively. The largest displacement before and after light stress for samples 602 and 604 are 0.40 and 0.106 which are good indicators for the two different porcine eyes elastic constants. Ocular rigidity obtained for the sample 602 and the sample 604 are: 2.20 and 1.80, respectively using the biphasic viscoelastic response. The exponential decay behaviors shown in the graph 600 can be used to correlate to the corneal elastic property as well. Additional corneal mechanical properties can be correlated to the exponential decay parameters.

The measured mechanical properties of the cornea can, thus, be provided for an eye doctor to study the relationship between particular eye diseases and these properties. In accordance with the present embodiments, a technologically significant system and method is provided which allows one to obtain the corneal elastic constant/rigidity parameter information rapidly, almost instant, reliably, non-invasively on a simple platform with no external introduced damages.

Thus, the present embodiments provide a method for analysing a property of a cornea of an eye using terahertz (THz) radiation by projecting a first THz wave onto a surface of the cornea and detecting a first reflected wave being a reflection of the first THz wave reflected from the surface of the cornea. The cornea is then deformed, a second THz wave onto the surface of the cornea after the deforming and the second reflected wave being a reflection of the second THz wave reflected from the surface of the cornea is detected after the deforming. The properties of the cornea are then calculated based on the first reflected wave and the second reflected wave.

The method further includes projecting a visible light to the surface of the cornea for less than ten seconds to induce light stress to the cornea so as to deform the cornea. The visible light can be generated by a light-pressure device placed at a distance of about one or two centimeters in front of the eye. The visible light can be a red light having a wavelength of 632 nm generated by the light-pressure device at a power of 100 µW Alternatively, air can be puffed to the surface of the cornea for less than ten seconds to induce stress to the cornea so as to deform the cornea.

Calculating the property of the cornea includes calculating an elastic property, c, of the cornea based on Equation (5).

$$F=cx \quad (5)$$

where x is derived from a peak position change in the first reflected wave and the second reflected wave and F is the light stress induced by the visible light, F being calculated by Equation (6):

$$F=(1+p)E/C \quad (6)$$

where p is a reflection coefficient of the surface of the cornea, E is incident energy flux of the visible light in W/m$^2$ and C is the speed of light in a vacuum. Calculating property of the cornea can also include calculating an elastic property, c, of the cornea based on Equation (7):

$$F=cx+nx'+mx'' \quad (7)$$

where x is derived from a peak position change in the first reflected wave and the second reflected wave, F is the light stress induced by the visible light, n is a damping factor of the cornea, m is the mass of the cornea, x' is a first order derivative of x, and x'' is a second order derivative of x, where F is calculated by Equation (7). The step of calculating the property of the cornea may also include calculating a rigidity property, G, of the cornea based on Equation (8):

$$c=2G(1+v) \quad (8)$$

where c is the elastic property of the cornea, and v represents a Poisson's ratio of the cornea.

When the first reflected wave has a peak position at a first time t1, and the second reflected wave has a peak position at a second time t2, x in Equations (5) or (7) can be calculated by Equation (9):

$$x = C \times (t2 - t1) \tag{9}$$

The visible light can be synchronized with the THz wave prior to detecting the second reflected wave by, possibly, projecting the visible light after the first reflected wave is detected. The deforming forms an elastic corneal deformation which may be a non-contact corneal deformation. In addition, the first THz wave and the second THz wave may have a same wavelength.

The method of the present embodiments can be performed by the systems described herein above and a processor may be provided to perform the synchronization, measurement and calculations of the methods of the present embodiments or computer readable medium may be provided which includes instructions which, when executed, will enable a system to perform a method for analysing a property of a cornea of an eye using terahertz (THz) radiation in accordance with the present embodiments.

Thus, it can be seen that the present embodiments provide systems and methods analysing a property of a cornea of an eye using terahertz (THz) radiation which provides a rapid, non-invasive, real-time corneal elastic/rigidity analysis. Such systems and methods can be applied in refractive surgery, which can be helpful for fine tuning typical parameter etching for an advanced LASIK procedure to achieve the better precision and successful rate.

While exemplary embodiments have been presented in the foregoing detailed description of the invention, it should be appreciated that a vast number of variations exist. It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of steps and method of operation described in the exemplary embodiment without departing from the scope of the invention as set forth in the appended claims.

What is claimed is:

1. A method for analysing a property of a cornea of an eye using terahertz (THz) radiation, the method comprising:
projecting a first THz wave onto a surface of the cornea;
detecting a first reflected wave being a reflection of the first THz wave reflected from the surface of the cornea;
deforming the cornea by projecting a visible light to the surface of the cornea for less than 10 seconds to induce light stress to the cornea;
projecting a second THz wave onto the surface of the cornea after the deforming;
detecting a second reflected wave being a reflection of the second THz wave reflected from the surface of the cornea after the deforming; and
calculating the property of the cornea based on the first reflected wave and the second reflected wave.

2. The method according to claim 1, further comprising: generating the visible light by a light-pressure device placed at a distance of between 1 to 2 cm in front of the eye.

3. The method according to claim 1, further comprising: puffing air to the surface of the cornea for less than 10 seconds to induce stress to the cornea so as to deform the cornea.

4. The method according to claim 1, wherein the visible light is a red light having a wavelength of 632 nm generated by the light-pressure device at a power of 100 μW.

5. The method according to claim 1, wherein the step of calculating the property of the cornea comprises: calculating an elastic property, c, of the cornea based on:

$$F = cx \tag{1}$$

wherein x is derived from a peak position change in the first reflected wave and the second reflected wave, and F is the light stress induced by the visible light, wherein F is calculated by:

$$F = (1+p)E/C \tag{2}$$

wherein p is reflection coefficient of the surface of the cornea, E is incident energy flux of the visible light in W/m², and C is light speed in vacuum.

6. The method according to claim 5, wherein the step of calculating the property of the cornea further comprises: calculating a rigidity property, G, of the cornea based on:

$$c = 2G(1+v) \tag{5}$$

wherein c is the elastic property of the cornea, and v represents a Poisson's ratio of the cornea.

7. The method according to claim 5, wherein the first reflected wave has a peak position at a first time t1, and the second reflected wave has a peak position at a second time t2, wherein x is calculated by:

$$x = C \times (t2 - t1) \tag{6}$$

wherein C is speed of light in a vacuum.

8. The method according to claim 1, wherein the step of calculating the property of the cornea comprises: calculating an elastic property, c, of the cornea based on:

$$F = cx + nx' + mx'' \tag{3}$$

wherein x is derived from a peak position change in the first reflected wave and the second reflected wave, F is the light stress induced by the visible light, n is a damping factor of the cornea, m is the mass of the cornea, x' is a first order derivative of x, and x'' is a second order derivative of x, wherein F is calculated by:

$$F = (1+p)E/C \tag{4}$$

wherein p is reflection coefficient of the surface of the cornea, E is incident energy flux of the visible light in W/m², and C is light speed in vacuum.

9. The method according to claim 1, further comprising: synchronizing the visible light with the first and second THz waves prior to detecting the second reflected wave.

10. The method according to claim 9, wherein the step of synchronizing the visible light with the first and second THz waves comprises: projecting the visible light after the first reflected wave is detected.

11. The method according to claim 1, wherein the deforming forms an elastic corneal deformation or a non-contact corneal deformation, and/or wherein the first THz wave and the second THz wave have a same wavelength.

12. A system for analysing a property of a cornea of an eye using terahertz (THz) radiation, the system comprising:
a device configured to deform the cornea, the device configured to deform the cornea comprising a light-pressure device configured to project a visible light to a surface of the cornea for less than 10 seconds to induce light stress to the cornea so as to deform the cornea;

a terahertz radiation measuring system comprising:
  a terahertz radiation generator configured to project a first THz wave and a second THz wave respectively before and after the corneal deforming, and
  a terahertz radiation detector configured to:
    detect a first reflected wave being a reflection of the first THz wave reflected from the surface of the cornea, and
    detect a second reflected wave being a reflection of the second THz wave reflected from the surface of the cornea after the deforming; and
  a signal processing unit configured to communicate with the terahertz radiation measuring system to calculate the property of the cornea based on the first reflected wave and the second reflected wave.

13. The system according to claim 12, wherein the light-pressure device is configured to be placed at a distance of between 1 to 2 cm in front of the eye, and wherein the visible light is a red light having a wavelength of 632 nm generated by the light-pressure device at a power of 100 μW.

14. The system according to claim 13, wherein the light-pressure device is configured to be synchronized with the terahertz radiation generator prior to the detector detecting the second reflected wave.

15. The system according to claim 14, wherein the light-pressure device is synchronized with the terahertz radiation generator so as to project the visible light after the detector detects the first reflected wave.

16. The system according to claim 12, wherein the terahertz radiation generator comprises:
  a femtosecond laser configured to generate the first THz wave and the second THz wave, and
  a terahertz radiation signal emitter configured to emit the first THz wave and the second THz wave onto the surface of the cornea respectively before and after the deforming, wherein the terahertz radiation signal emitter is an antenna or a nonlinear crystal.

17. The system according to claim 16, further comprising an optical system comprising two off-axis parabolic (OAP) mirrors,
  wherein a first mirror of the two OAP mirrors is arranged in an optical path of the terahertz radiation generator and is configured to receive the first THz wave and the second THz wave emitted from the terahertz radiation signal emitter and reflect at least a portion of the first THz wave and the second THz wave to be projected onto the surface of the cornea; and
  wherein a second mirror of the two OAP mirrors is configured to be arranged in a symmetrical position to the first mirror with respect to the eye and is configured to receive at least a portion of the first THz wave and the second THz wave reflected from the cornea to provide return beams respectively for the first THz wave and the second THz wave.

18. The system according to claim 16, further comprising a THz wave detector arranged in an optical path of the return beams so as to receive the first reflected wave and the second reflected wave, respectively, wherein the terahertz wave detector is an antenna or a nonlinear crystal.

19. The system according to claim 12, wherein the signal processing unit is configured to calculate an elastic property, c, of the cornea based on:

$$F=cx \quad (1),$$

wherein x is derived from a peak position change in the first reflected wave and the second reflected wave, and F is the light stress induced by the visible light, wherein F is calculated by:

$$F=(1+p)E/C \quad (2),$$

wherein p is reflection coefficient of the surface of the cornea, E is incident energy flux of the visible light in W/m$^2$, and C is light speed in vacuum.

20. The system according to claim 19, wherein the signal processing unit is further configured to calculate a rigidity property, G, of the cornea based on:

$$c=2G(1+v) \quad (5),$$

wherein c is the elastic property of the cornea, and v represents a Poisson's ratio of the cornea.

21. The system according to claim 19, wherein the first reflected wave has a peak position at a first time t1, and the second reflected wave has a peak position at a second time t2, wherein x is calculated by:

$$x=C \times (t2-t1) \quad (6),$$

wherein C is speed of light in a vacuum.

22. The system according to claim 12, wherein the signal processing unit is configured to calculate an elastic property, c, of the cornea based on:

$$F=cx+nx'+mx'' \quad (3),$$

wherein x is derived from a peak position change in the first reflected wave and the second reflected wave, F is the light stress induced by the visible light, n is a damping factor of the cornea, m is the mass of the cornea, x' is a first order derivative of x, and x'' is a second order derivative of x, wherein F is calculated by:

$$F=(1+p)E/C \quad (4),$$

wherein p is reflection coefficient of the surface of the cornea, E is incident energy flux of the visible light in W/m$^2$, and C is light speed in vacuum.

* * * * *

UNITED STATES PATENT AND TRADEMARK OFFICE
CERTIFICATE OF CORRECTION

| | | |
|---|---|---|
| PATENT NO. | : 12,161,413 B2 | Page 1 of 1 |
| APPLICATION NO. | : 17/260218 | |
| DATED | : December 10, 2024 | |
| INVENTOR(S) | : Lin Ke et al. | |

It is certified that error appears in the above-identified patent and that said Letters Patent is hereby corrected as shown below:

In the Specification

In Column 1, Line 14, delete "10/201,806046S" and insert --10201806046S--.

Signed and Sealed this
Twenty-fifth Day of November, 2025

John A. Squires
*Director of the United States Patent and Trademark Office*